United States Patent
Merrick et al.

(10) Patent No.: US 6,467,478 B1
(45) Date of Patent: *Oct. 22, 2002

(54) GAS MIXING APPARATUS FOR A VENTILATOR

(76) Inventors: Edwin B. Merrick, 274 W. Action Rd., Stow, MA (US) 01775; Glen N. Gee, 2200 Faraday Ave., Carlsbad, CA (US) 92008; John O'Mahony, 70 Hazel Park, Newcastle, Galway (IE); John O'Dea, 66 Westbrook, Knocknacarra, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 09/598,287

(22) Filed: Feb. 2, 2000

Related U.S. Application Data

(63) Continuation of application No. 09/277,528, filed on Mar. 26, 1999, now Pat. No. 6,116,240, which is a continuation of application No. 08/878,336, filed on Jun. 18, 1997, now Pat. No. 5,934,274, which is a continuation of application No. 08/688,868, filed on Jul. 31, 1996, now Pat. No. 5,664,560, which is a continuation of application No. 08/385,951, filed on Feb. 8, 1995, now abandoned.

(51) Int. Cl.$^7$ .............................................. A61M 16/00
(52) U.S. Cl. .............................. 128/203.25; 128/205.18
(58) Field of Search ....................... 128/203.25, 203.12, 128/204.18, 204.21, 204.22, 204.29, 204.25, 204.28, 205.11, 205.13–205.18; 417/259, 262, 267

(56) References Cited

U.S. PATENT DOCUMENTS

| | | | |
|---|---|---|---|
| 1,488,171 A | 3/1924 | Savidge | |
| 1,498,471 A | 6/1924 | Miller | |
| 3,527,213 A | 9/1970 | Schreiber | |
| 3,599,633 A | 8/1971 | Beasley | |
| 3,889,669 A | 6/1975 | Weigl | |
| 4,023,587 A | 5/1977 | Dobritz | |
| 4,121,578 A | 10/1978 | Torzala | |
| 4,340,044 A | 7/1982 | Levy et al. | |
| 4,380,233 A | 4/1983 | Caillot | |

(List continued on next page.)

FOREIGN PATENT DOCUMENTS

| | | |
|---|---|---|
| CA | 1319175 | 6/1993 |
| DE | 213 076 | 8/1984 |
| EP | 0 042 321 | 12/1981 |
| EP | 0 056 148 | 7/1982 |
| JP | 2-102383 | 4/1990 |

OTHER PUBLICATIONS

Younes, et al., "Proportional Assist Ventilation", Am. Rev. Resp. Dis., 1992, 145, pp. 121–129.

Primary Examiner—John G. Weiss
Assistant Examiner—Teena Mitchell

(57) ABSTRACT

The gas mixing apparatus provides the components of a breathing gas for mixing at approximately ambient atmospheric pressure, and regulates the pressure of a selected gas to approximately ambient atmospheric pressure for mixing with air at ambient atmospheric pressure. The gas mixing apparatus includes a piston disposed within a pump chamber. A flow limiting inlet controls introduction of a first selected gas such as oxygen for mixing with a second selected gas such as air. The pressure of the first selected gas is limited to an acceptable maximum pressure, so that even if a valve for admitting the first selected gas for mixing at ambient pressure fails, breathing gas will not be provided at an excessive pressure. A demand valve is alternatively provided for reducing the pressure of the first selected gas supplied before mixing, but a pressure sensor is also provided downstream of the demand valve for detecting failure of the demand valve, to shut off the supply of the first selected gas to prevent overpressurization.

4 Claims, 5 Drawing Sheets

U.S. PATENT DOCUMENTS

| | | | | |
|---|---|---|---|---|
| 4,401,115 A | * | 8/1983 | Monnier | 128/204.23 |
| 4,587,967 A | | 5/1986 | Chu et al. | |
| 4,702,240 A | | 10/1987 | Chaoui | |
| 4,823,593 A | | 4/1989 | Furlong et al. | |
| 4,832,014 A | | 5/1989 | Perkins | |
| 4,932,401 A | | 6/1990 | Perkins | |
| 5,014,694 A | | 5/1991 | DeVries | |
| 5,107,830 A | | 4/1992 | Younes | |
| 5,237,990 A | | 8/1993 | Psaros et al. | |
| 5,299,568 A | | 4/1994 | Forare et al. | |
| 5,664,560 A | * | 9/1997 | Merrick et al. | 128/203.25 |
| 6,116,240 A | * | 9/2000 | Merrick et al. | 128/203.25 |

* cited by examiner

GAS MIXING APPARATUS FOR A VENTILATOR

RELATED APPLICATIONS

This is a continuation of Ser. No. 09/277,528 filed Mar. 26, 1999 now U.S. Pat. No. 6,176,240, which was a continuation of Ser. No. 08/878,336, filed Jun. 18, 1997, now U.S. Pat. No. 5,934,274, which was a continuation of Ser. No. 08/688,868 filed Jul. 31, 1996, now U.S. Pat. No. 5,664,560, which is a continuation of Ser. No. 08/385,951 filed Feb. 8, 1995, abandoned.

BACKGROUND OF THE INVENTION

1. Field of the Invention

This invention relates generally to apparatus for mixing breathing gas for ventilating the lungs of a patient, and more particularly concerns apparatus suitable for use with a piston type ventilator, for delivering gas to the piston chamber of the ventilator at or near atmospheric pressure, without the need for a compressor, and a method for limiting the peak flow of oxygen supplied to the piston chamber of the ventilator.

2. Description of Related Art

Medical ventilators are designed to ventilate a patient's lungs with breathing gas to assist a patient in breathing when the patient is somehow unable to adequately breath on his own. Some ventilator systems in the art provide the patient with pressure assistance that is instituted when the patient has already begun an inspiratory effort. Such a ventilator provides an increase in pressure of the breathing gas in the patient airway to assist the flow of breathing gas to the patient's lungs, thus decreasing the work of breathing by the patient. Conventional pressure controlled ventilator systems implement a gas flow control strategy of terminating breathing gas flow when a target pressure is reached, or after a specified delay at this target pressure.

However, such a control strategy can result in over-pressurization of the patient's lungs, particularly when high pressure gasses are used for blending the breathing gas mixture, due to the response time delay in reducing pressure after a target pressure is sensed, or after a specified elapsed time. When over-pressurization is sustained, the patient's lungs can be subjected to excessive pressure for a significant portion of a breath cycle. When this occurs, the possibility exists that the patient will be harmed by a higher than desirable pressure in the lungs, since overpressure can, for example, rupture sutures or blood vessels of a patient that has recently undergone thoracic or abdominal surgery. Similarly, frail or infirm patients, such as asthmatic or emphysemic patients, can also be harmed if airway pressure is excessive.

Bellows and piston types of ventilators allow delivery of a predetermined volume of breathing gas at a desired pressure responsive to the initiation of inspiratory efforts by a patient. Piston based ventilators can typically be made to be more compact than bellows based ventilators, but piston ventilators typically blend pressurized air and oxygen in a high pressure blender. The resultant mixture is then drawn by a piston through a valve that reduces the pressure of the mixture. Such systems typically do not permit the use of room air and pressurized oxygen, and can result in some risk of overpressurization in the event of failure of a high pressure gas delivery valve controlling introduction of one of the breathing gas components into the high pressure blender.

For example, one piston based lung ventilator known in the art utilizes a rolling-seal piston of low inertia and low frictional resistance for delivery of breathing gas, which is mixed in the piston chamber. For mixing of the breathing gas in the piston chamber, the piston chamber has an outlet connected to the airway of the patient, and an inlet with a one-way valve allows air to enter the piston chamber during the exhalation phase of the respiratory cycle. This inlet to the piston chamber, controlled by a solenoid valve, allows introduction of a desired gas mixture into the piston chamber. The solenoid valve for introducing the gas mixture is opened during expiration as the piston reciprocates to a baseline position. The oxygen content of the inspired gas can also be enriched by admitting a continuous flow of oxygen into the piston chamber through another inlet.

In another gas blender for a ventilator, a double ended poppet cooperates with two valve seats to simultaneously open and close both valves to maintain a constant flow ratio. However, in both instances the gases mixed are supplied at high pressure. If a valve controlling the introduction of high pressure oxygen or air fails, it is possible that breathing gas can be provided to a patient at an excessive pressure. In addition, with these types of systems for introducing different gases into a gas delivery cylinder of a ventilator, mixing of the gases can be incomplete, sometimes resulting in delivery of a lower concentration of oxygen to a patient than desired.

It would therefore be desirable to provide the components of a breathing gas for mixing, such as oxygen and air, at approximately ambient atmospheric pressure. An advantage of such an arrangement is that air can readily be supplied from the ambient atmosphere without the necessity of providing a compressor equipment for providing pressurized air. It would be desirable to regulate the pressure of a selected gas, such as oxygen, to approximately ambient pressure, for mixing with ambient pressure air. It would further be desirable to limit the pressure of the selected gas to be mixed with ambient pressure air to an acceptable maximum pressure, so that even if a valve for admitting the selected gas at ambient pressure for mixing fails, breathing gas will not be provided at an excessive pressure. It would also be desirable to provide a gas mixing apparatus that would allow a desired sequencing of introduction of the selected gases to be mixed into a gas delivery cylinder of a ventilator. The present invention meets these needs.

SUMMARY OF THE INVENTION

Briefly, and in general terms, the present invention provides for a gas mixing apparatus for a ventilator system for providing the components of a breathing gas for mixing at approximately ambient atmospheric pressure, and that regulates the pressure of a selected gas to approximately ambient atmospheric pressure, for mixing with air at ambient atmospheric pressure. The gas mixing apparatus limits the pressure of the selected gas to an acceptable maximum pressure, so that even if a valve for admitting the selected gas for mixing at ambient pressure fails, breathing gas will not be provided at an excessive pressure.

In one preferred embodiment, the gas mixing apparatus comprises a fixed volume piston chamber having a first gas delivery portion of the piston chamber with an inlet for receiving mixed gas and an outlet for delivering mixed gas to the patient airway during an inspiratory portion of a breath cycle. A reciprocating piston is disposed within the piston chamber, movable between an extended position in the first gas delivery portion of the piston chamber and a retracted position in a second portion of the piston chamber. Means are provided for moving the piston between the extended and retracted positions, and in one preferred aspect of the invention, a reservoir can provide a mixing chamber for mixing a selected gas, such as oxygen, with air, while in another preferred embodiment the selected gas is mixed in a mixing chamber of the piston chamber.

In each embodiment, the mixing chamber preferably includes an air inlet open to the atmosphere, and a flow limiting inlet for admitting the selected gas into the mixing chamber. In one preferred aspect of the invention, the flow limiting inlet comprises a regulator and a sonic orifice allowing a maximum mass flow rate of the selected gas to the mixing chamber. A source of the selected gas is provided for supplying a flow of the selected gas to the mixing chamber, and valve means are provided in fluid communication with the source and the mixing chamber for regulating the flow of the selected gas to the mixing chamber. The gas mixing apparatus also preferably includes control means for controlling the valve means to admit the selected gas to the mixing chamber during at least one interval of time during at least a portion of the breath cycle for a total period of time during the breath cycle to obtain a selected proportion of the selected gas in the mixed gas.

In a first presently preferred embodiment, the mixing chamber comprises at least one reservoir connected in fluid communication with the inlet of the piston chamber, and in another preferred embodiment, the mixing chamber can comprise a plurality of reservoirs or reservoir chambers connected in series in fluid communication with the inlet of the piston chamber. In another preferred embodiment, the mixing chamber comprises a gas mixing portion of the piston chamber between the piston and the second side of the piston chamber.

In another preferred aspect of the invention, although air is supplied at ambient atmospheric pressure, the selected gas is supplied at a pressure above atmospheric pressure, and the gas mixing apparatus further includes a demand valve for reducing the pressure of the selected gas supplied to atmospheric pressure. A pressure sensor is preferably provided upstream of the demand valve for sensing a low supply of the selected gas, and a pressure sensor is preferably provided downstream of the demand valve for detecting failure of the demand valve, and generates a failure signal when failure of the demand valve is detected. A solenoid valve upstream of the demand valve responsive to the failure signal of the downstream pressure sensor is provided to close off the supply flow of the selected gas, preventing excessive pressure buildup of the selected gas from reaching the mixing chamber and preventing overpressurization of the patient airway.

The invention also provides for a method of mixing gas for a ventilator system used for supplying mixed breathing gas to a patient airway during an inspiratory portion of a breath cycle. In a presently preferred method according to the invention, a supply flow of a first selected gas is provided for mixing with a second selected gas. The piston is moved to an extended position to deliver a flow of mixed gas from the gas delivery portion of the piston chamber to the patient airway; and is moved to a retracted position to draw mixed gas into the gas delivery portion of the piston chamber. The supply flow of the first selected gas is controlled to admit the first selected gas for mixing during at least one interval of time period during the breath cycle, and for a total period of time during the breath cycle, to obtain a selected proportion of the first selected gas in the mixed gas.

One preferred embodiment of the method of the invention involves admitting mixed gas during retraction of the piston; and another preferred embodiment of the method of the invention involves admitting mixed gas during extension of the piston to deliver mixed gas to the patient airway. In another preferred embodiment of the method of the invention, introduction of the selected gas and air into a gas delivery chamber is sequenced in the mixing cycle, with a pulse of the selected gas followed by a pulse of air, to help insure adequate mixing of the selected gas and air for delivery to a patient.

From the above, it may be seen that the present invention provides an improved method and apparatus for providing mixed breathing gas for a patient being ventilated by a piston type ventilator. These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
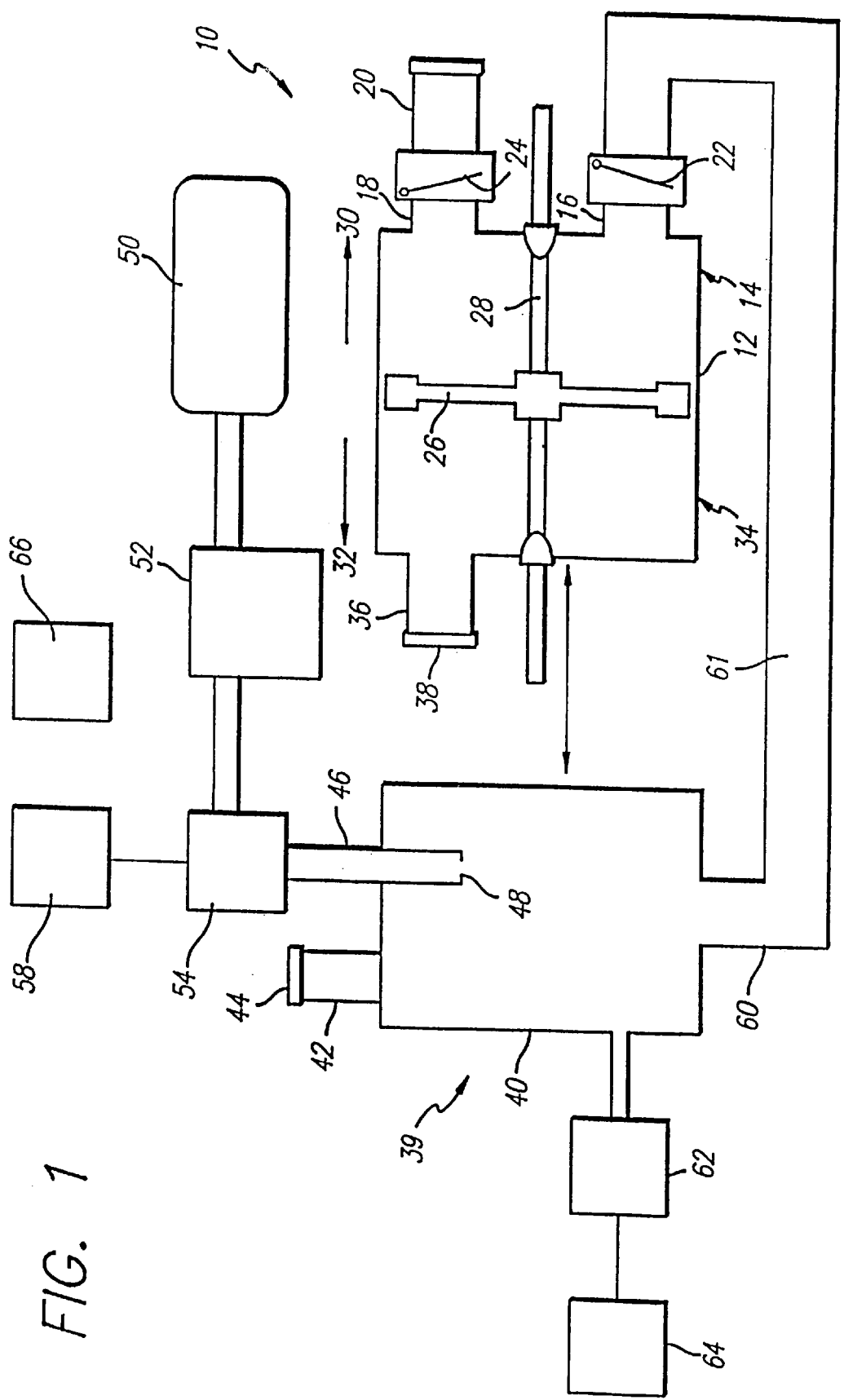
FIG. 1 is a schematic diagram of a first preferred embodiment of the gas mixing apparatus of the invention in which the gas mixing chamber is a single reservoir.

Ventilator systems generally provide a patient with breathing gas under elevated pressure when the patient begins an inspiratory effort, terminating pressurized breathing gas flow when the target pressure is reached, or other termination criteria have been satisfied. However, when high pressure gasses are used for blending the breathing gas mixture, a patient may receive breathing gas at dangerously high pressures. Piston based ventilators typically blend pressurized air and oxygen in a high pressure blender, which can result in overpressurization in the event of failure of a high pressure gas delivery valve controlling introduction of one of the breathing gas components into the high pressure blender, or the device controlling introduction of low pressure gas to the cylinder. The gas mixing apparatus is particularly suited to a piston type ventilator, for delivering gas to the piston chamber at or near atmospheric pressure. In the method of the invention, the supply flow of the selected gas to the mixing chamber is controlled to admit the selected gas to the mixing chamber during at least one interval of time period during the breath cycle, and for a total period of time during the breath cycle, to obtain a selected proportion of the selected gas in the mixed gas. By sequencing introduction of pulses of the selected gas and air into a gas delivery chamber in the mixing cycle, adequate mixing of the selected gas and air is facilitated.

As is illustrated in the drawings, the invention provides for a gas mixing apparatus for a ventilator system for mixing the components of a breathing gas at approximately ambient atmospheric pressure. The pressure of a selected gas to be mixed in the breathing gas is regulated to be approximately 14.7 psig. Furthermore, the pressure of the selected gas is limited to an acceptable maximum pressure, so that even if a valve for admitting the selected gas at ambient pressure fails, breathing gas will not be provided at an excessive pressure.

In a first preferred embodiment, shown in FIG. 1, the gas mixing apparatus 10 includes a fixed volume piston chamber 12 having a first gas delivery portion 14 with an inlet 16 for receiving mixed gas and an outlet 18 for delivering mixed gas to the patient airway 20 during an inspiratory portion of a breath cycle. The inlet includes a check valve 22 allowing one way flow of the mixed gas into the piston chamber; and the outlet similarly has a check valve 24 allowing one way flow of the mixed gas to the patient airway. A reciprocating piston 26 mounted to a piston rod 28 connected to means for moving the piston, such as a rack and pinion motor (not shown), is disposed within the piston chamber, and is movable within the piston chamber between an extended position 30 in the first gas delivery portion 14 of the piston chamber and a retracted position 32 in a second portion 34 of the piston chamber on the opposite side of the piston from first gas delivery portion 14 of the piston chamber. The second portion 34 of the piston chamber preferably includes a vent 36, with a filter 38, open to the atmosphere.

Figure 2:
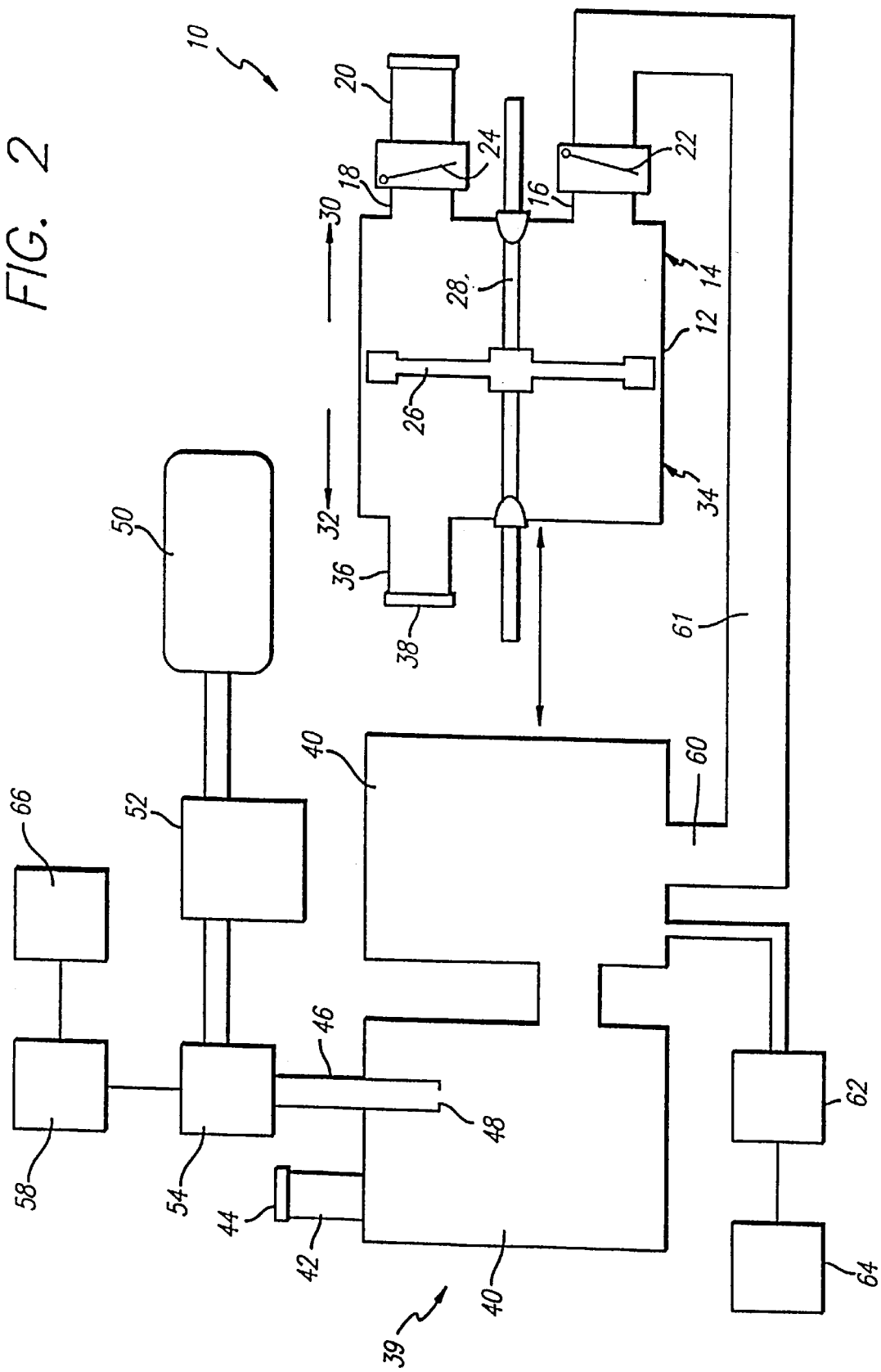
FIG. 2 is a schematic diagram of an alternate preferred embodiment of the gas mixing apparatus of the invention in which the gas mixing chamber includes multiple reservoirs.

The gas mixing apparatus also includes gas mixing chamber means 39, which in the first preferred embodiment comprises at least one reservoir or reservoir chamber 40 for mixing a selected gas with air, with at least one reservoir having an air inlet 42, typically provided with a filter 44, and otherwise open to the ambient atmosphere for admitting air to the reservoir. As is shown in FIG. 1, the reservoir 40 is connected in fluid communication with the inlet 16 of the piston chamber, as will be further explained below. Alternatively, as is illustrated in FIG. 2, which is substantially similar in all other respects to the configuration of FIG. 1, the reservoir can also comprise a plurality of reservoirs or reservoir chambers 40 connected in series in fluid communication with the inlet 16 of the piston chamber, although such multiple reservoirs can also be connected in parallel.

The reservoir also preferably includes a flow limiting inlet 46 for admitting the selected gas to the reservoir. The flow limiting inlet preferably comprises a sonic flow limiting orifice 48 allowing a maximum mass flow rate of the selected gas to the reservoir, provided that the ratio of upstream to downstream pressure is typically greater than about 2. The sonic flow limiting orifice is of the commonly known type of orifice that limits the speed of flow of fluid through the orifice to less than the speed of sound in the fluid, allowing for a constant mass flow rate upstream of the orifice despite downstream pressure variations. Oxygen flow rate is advantageously limited to an absolute maximum by the sonic flow limiting orifice.

A source 50 of the selected gas is also provided, such as a tank of pressurized oxygen, for example, for supplying a flow of the selected gas to the reservoir. Gas pressure regulating means 52 is preferably connected in fluid communication to the high pressure source 50 of the selected gas for regulating the pressure of the gas supplied from the selected gas source, as will be further explained below. Valve means 54 for controlling the flow of the selected gas to the reservoir, such as a solenoid valve, is provided in fluid communication between the pressure regulating means 52 and the flow limiting inlet 46 to the reservoir. The valve means is switchable between an open position in which the selected gas flows to the reservoir, and a closed position in which the selected gas is prevented from flowing to the reservoir. A control unit 58, typically connected to sensors (not shown) for monitoring the patient breathing cycle, is also preferably provided for controlling the valve means 54 to admit the selected gas into the reservoir during at least one interval of time during at least a portion of the breath cycle for a total period of time to obtain a selected proportion of the selected gas in the mixed gas, typically preset or selected through the control unit.

The reservoir also includes an outlet 60 in fluid communication through conduit 61 with the inlet 16 to the piston chamber, so that after extension of the piston in the piston chamber to deliver gas to the patient airway, the piston moves to a retracted position during patient exhalation, returning to a base position, drawing mixed gas from the reservoir into the piston chamber. The solenoid valve is typically opened for a sufficient time to supply the desired proportion of oxygen in the mixed gas supplied to the piston chamber. The time during which the solenoid valve is switched open can be 100% of the time period in which the piston is retracting, and the reservoir means is being filled with gas, to produce 100% oxygen. If the solenoid valve is switched open 25% of the retraction period, a mixture is produced having about a 41% oxygen concentration. The concentration of the selected gas can be corrected for atmospheric changes by sensing atmospheric pressure changes with a pressure sensor, and a microprocessor, for example, that is responsive to signals from the pressure sensor to adjust the time that the solenoid valve is switched open. The movement of the reciprocating piston in the piston chamber is controlled by the control unit to deliver a quantity of mixed gas in the desired volume at the desired pressure to a patient.

By utilizing a flow limiting inlet for the selected gas, if the solenoid valve controlling the supply flow of the selected gas to the reservoir fails, and is stuck open, the selected gas will flow at the maximum rate allowed by the flow limiting inlet to the reservoir. Excess flow is vented to the atmosphere back through air vent 42 of the reservoir means, so that the failure will not result in excess pressure applied to the patient. If the solenoid valve is stuck closed, the supply of selected gas will not flow, but the patient will be ventilated with room air. In either case, a sensor 62 of the concentration of the selected gas in the mixed breathing gas can be provided, such as in the reservoir, or in the patient airway, for example, to operate an alarm 64 to alert an operator so that the problem can be corrected.

During retraction of the piston (typically occurring during patient exhalation), the pressure in the reservoir chamber is nearly at atmospheric pressure. As will be explained further hereinbelow, an upstream gas supply gauge pressure of 14.7 psig can provide a 2 to 1 ratio of absolute pressures, thus ensuring that sonic flow conditions are met. Allowing for pressure drops in the system, a pressure regulator is set to control output of the gas source to about 28.5 psig to ensure that the upstream requirement of 14.7 psig is met in all atmospheric conditions. Atmospheric pressure sensing means 66 can also be provided and connected to the control unit, to monitor the actual ambient atmospheric pressure, for adjusting the total period of time of admitting the selected gas to the reservoir means to compensate for variations in atmospheric pressure to obtain the selected proportion of the selected gas in the mixed gas.

Figure 3:
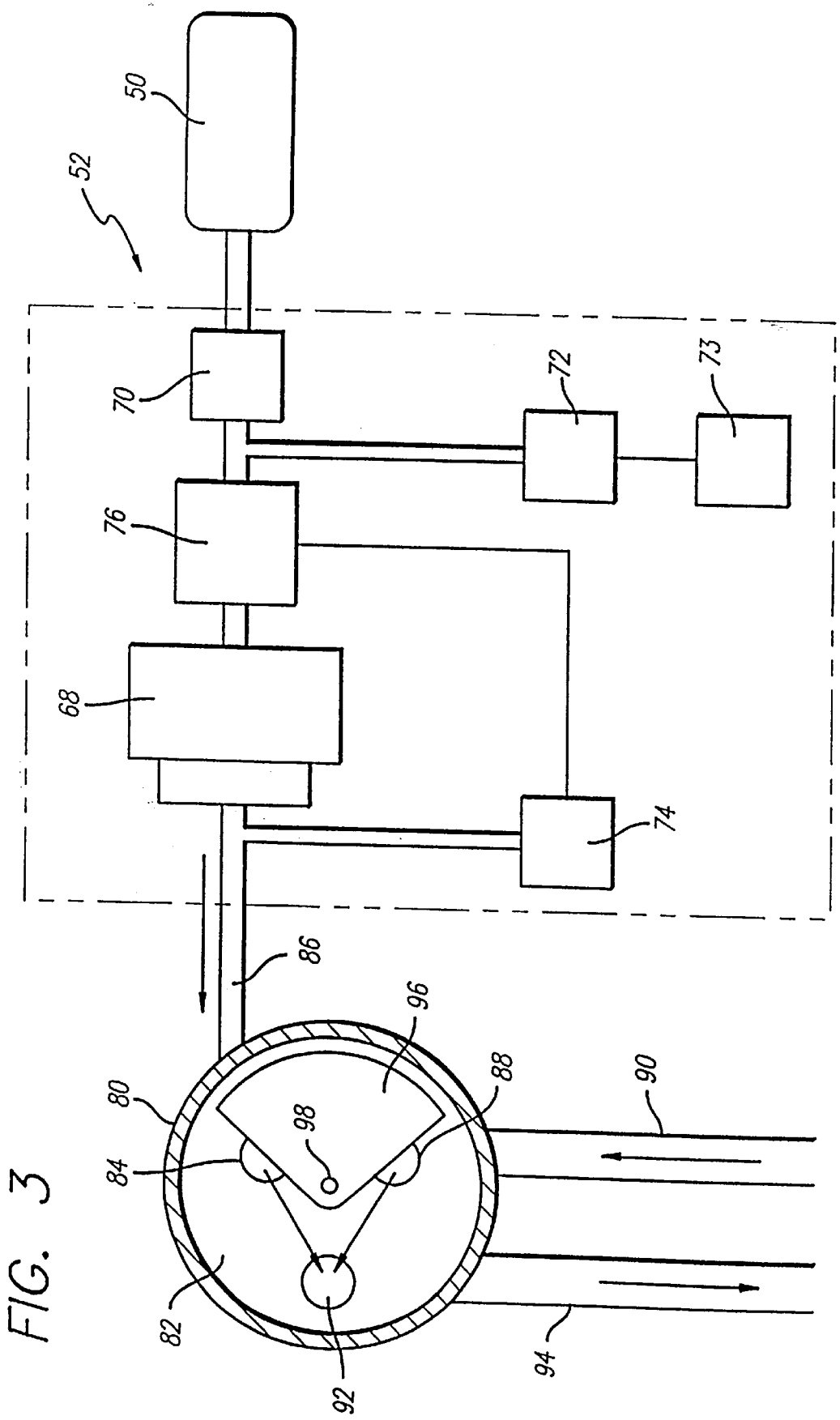
FIG. 3 is a schematic diagram of the selected gas supply pressure regulating means of the gas mixing apparatus of the invention.

As is illustrated in FIG. 3, the pressure regulating means 52 provided for this purpose can in one preferred embodiment employ a demand valve 68 for reducing the pressure of the selected gas supplied from source 50 to atmospheric pressure. The selected gas is typically oxygen, stored in the source tank at a pressure of approximately 200 bar, and is supplied through a pressure regulator 70 connected to the source tank at approximately 30–100 psi output. A pressure sensor 72, such as a pressure sensitive switch triggered when the supply pressure falls below about 30 psig, is positioned upstream of the demand valve, between the demand valve and the pressure regulator 70, to signal low oxygen supply, such as an alarm 73. Another pressure sensor 74, such as a pressure switch triggered when the gas pressure rises above about 30 cm $H_2O$, is positioned downstream of the demand valve, to detect an open failure of the demand valve. The demand valve monitoring pressure sensor 74 is connected via control means to a solenoid valve 76 positioned in the selected gas supply line to the reservoir to regulate flow to the cylinder. When failure of the demand valve is detected by the sensor, the demand valve pressure sensor 74 generates a signal causing solenoid valve 76, typically upstream of the demand valve, to close when the demand valve fails, shutting off the oxygen supply, preventing oxygen under excessive pressure from reaching the mixing chamber and the patient airway.

The air and the oxygen supplied at approximately atmospheric pressure can, in one currently preferred embodiment, be introduced into a blender 80 that controls the mixture by providing mechanically adjustable resistance in the air and oxygen paths. The blender 80 includes an interior chamber 82 having a first inlet 84 for introducing a first selected gas, such as oxygen, received from the demand valve 68 through line 86, and a second inlet 88, for admitting a second selected gas, such as air, such as from line 90. The blender also includes an outlet 92 for conducting the blended first and second gases through the outlet line 94 to the piston chamber, or to one or more reservoirs leading to the piston chamber. The blender also includes a movable plate 96 that can be moved to cover all or a portion of one or both inlets 84 and 88 to offer a mechanically adjustable resistance in the paths of the first and second gases to the outlet. The plate 96 can, for example be mounted in the blender to rotate about a pivot point 98, so as to cover or uncover the inlets as desired to control the proportions of the gases being mixed.

Figure 4:
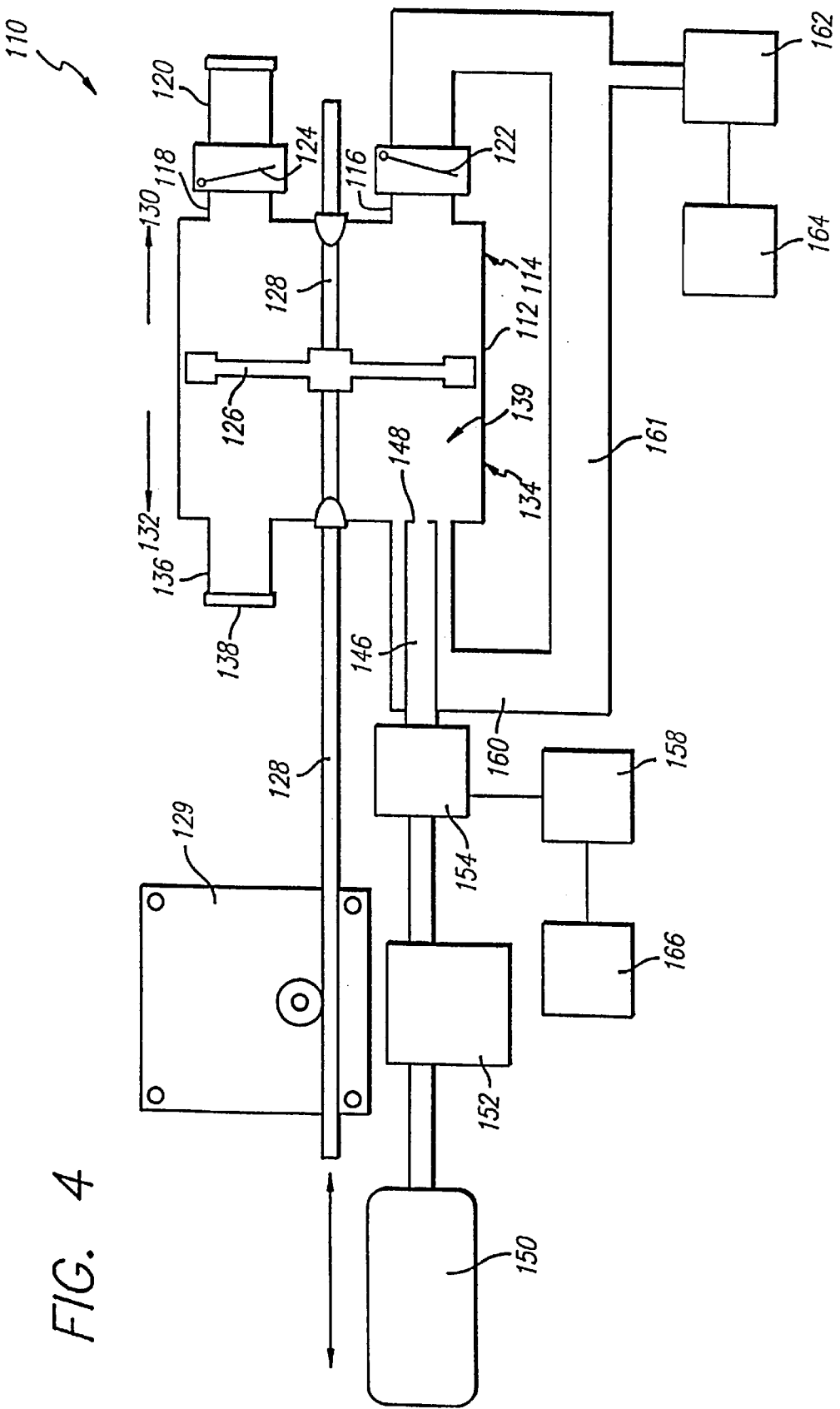
FIG. 4 is a schematic diagram of another preferred embodiment of the gas mixing apparatus of the invention in which the gas mixing chamber is incorporated in the piston chamber.

As is illustrated in FIG. 4, in a second preferred embodiment, the gas mixing apparatus 110 includes a fixed volume piston chamber 112 with a first gas delivery portion 114, an inlet 116 for receiving mixed gas, and an outlet 118 for delivering mixed gas to the patient airway 120. The inlet includes a check valve 122 allowing mixed gas to flow in only one direction, into the piston chamber. The outlet also includes a check valve 124 allowing mixed gas to flow only to the patient airway. A reciprocating piston 126 mounted to a piston rod 128 that is connected a rack and pinion motor 129 for moving the piston, is disposed within the piston chamber, and is movable within the piston chamber between an extended position 130 in the first gas delivery portion 114 of the piston chamber and a retracted position 132 in a second portion 134 of the piston chamber on the opposite side of the piston from first gas delivery portion 114 of the piston chamber. The second portion 134 of the piston chamber preferably includes an air inlet 136, with a filter 138, open to the atmosphere.

In the second preferred embodiment, the gas mixing chamber 139 is provided in the second portion 134 of the piston chamber, eliminating the requirement for a separate reservoir, and thereby making the gas mixing apparatus considerably more compact. As is shown in FIG. 4 and will be further explained below, the gas mixing chamber 139 is connected in fluid communication with the inlet 116 of the piston chamber.

The gas mixing chamber 139 also preferably includes a flow limiting inlet 146 for admitting the selected gas to the gas mixing chamber. The flow limiting inlet preferably comprises a sonic flow limiting orifice 148 allowing a maximum mass flow rate of the selected gas to the gas mixing chamber, provided that the ratio of upstream to downstream pressure is typically greater than about 2. The sonic flow limiting orifice is of the commonly known type of orifice that limits the speed of flow of fluid through the orifice to less than the speed of sound in the fluid, allowing for a constant mass flow rate upstream of the orifice despite downstream pressure variations. Oxygen flow rate is advantageously limited to an absolute maximum by the sonic flow limiting orifice.

A source 150 of the selected gas is also provided, such as a tank of pressurized oxygen, for example, for supplying a flow of the selected gas to the gas mixing chamber. Gas pressure regulating means 52 is preferably connected in fluid communication to the high pressure source 150 of the selected gas for regulating the pressure of the gas supplied from the selected gas source. The pressure regulating means 52 shown in FIG. 4 is substantially identical to the pressure regulating means 52 of FIG. 1 and can equally comprise the demand valve arrangement 52 and blender 80 as described above with reference to FIG. 3. Valve means 154 for regulating the flow of the selected gas to the gas mixing chamber, such as a solenoid valve, is provided in fluid communication between the pressure regulating means 52 and the flow limiting inlet 146 to the gas mixing chamber. The valve means is switchable between an open position in which the selected gas flows to the gas mixing chamber, and a closed position in which the selected gas is prevented from flowing to the gas mixing chamber. A control unit 158, typically connected to sensors (not shown) for monitoring the patient breathing cycle, is also preferably provided for controlling the valve means 154 to admit the selected gas to the gas mixing chamber during at least one interval of time during at least a portion of the breath cycle for a total period of time to obtain a selected proportion of the selected gas in the mixed gas, typically preset or selected through the control unit.

The gas mixing chamber also includes an outlet 160 in fluid communication through conduit 161 with the inlet 116 to the piston chamber, so that after extension of the piston in the piston chamber to deliver gas to the patient airway, the piston moves to a retracted position during patient exhalation, returning to a base position, drawing mixed gas from the gas mixing chamber into the gas delivery side of the piston chamber. The solenoid valve is typically opened for a sufficient time to supply the desired proportion of oxygen in the mixed gas supplied to the piston chamber. The concentration of the selected gas can be corrected for atmospheric changes by sensing atmospheric pressure changes with a pressure sensor, and a microprocessor, for example, that is responsive to signals from the pressure sensor to adjust the time that the solenoid valve is switched open. The movement of the reciprocating piston in the piston chamber is controlled by the control unit to deliver a quantity of mixed gas in the desired volume at the desired pressure to a patient.

Utilizing a flow limiting inlet for the selected gas such as the sonic flow limiting orifice in the gas mixing apparatus, if the solenoid valve controlling the supply flow of the selected gas to the gas mixing chamber fails, and is stuck open, the selected gas will flow at the maximum rate allowed by the flow limiting inlet to the gas mixing chamber. Excess flow is vented to the atmosphere back through air vent 136 to the gas mixing chamber so that the failure will not result in excess pressure applied to the patient. If the solenoid valve is stuck closed, the supply of selected gas will not flow, but the patient will be ventilated with room air. In either case, a sensor 162 of the concentration of the selected gas in the mixed breathing gas can be provided, such as in the gas mixing chamber, in the line 161 between the gas mixing chamber and the gas delivery portion of the piston chamber, or in the patient airway, for example, to operate an alarm 164 to alert an operator so that the problem can be corrected.

During retraction of the piston, which typically occurs during patient exhalation, the pressure in the gas mixing chamber is nearly at atmospheric pressure. As will be explained further hereinbelow, an upstream gas supply gauge pressure of 14.7 psig can provide a 2 to 1 ratio of absolute pressures. Atmospheric pressure sensing means 166 can also be provided and connected to the control unit, to monitor the actual ambient atmospheric pressure, for adjusting the total period of time of admitting the selected gas to the gas mixing chamber to compensate for variations in atmospheric pressure to obtain the selected proportion of the selected gas in the mixed gas.

Figure 5:
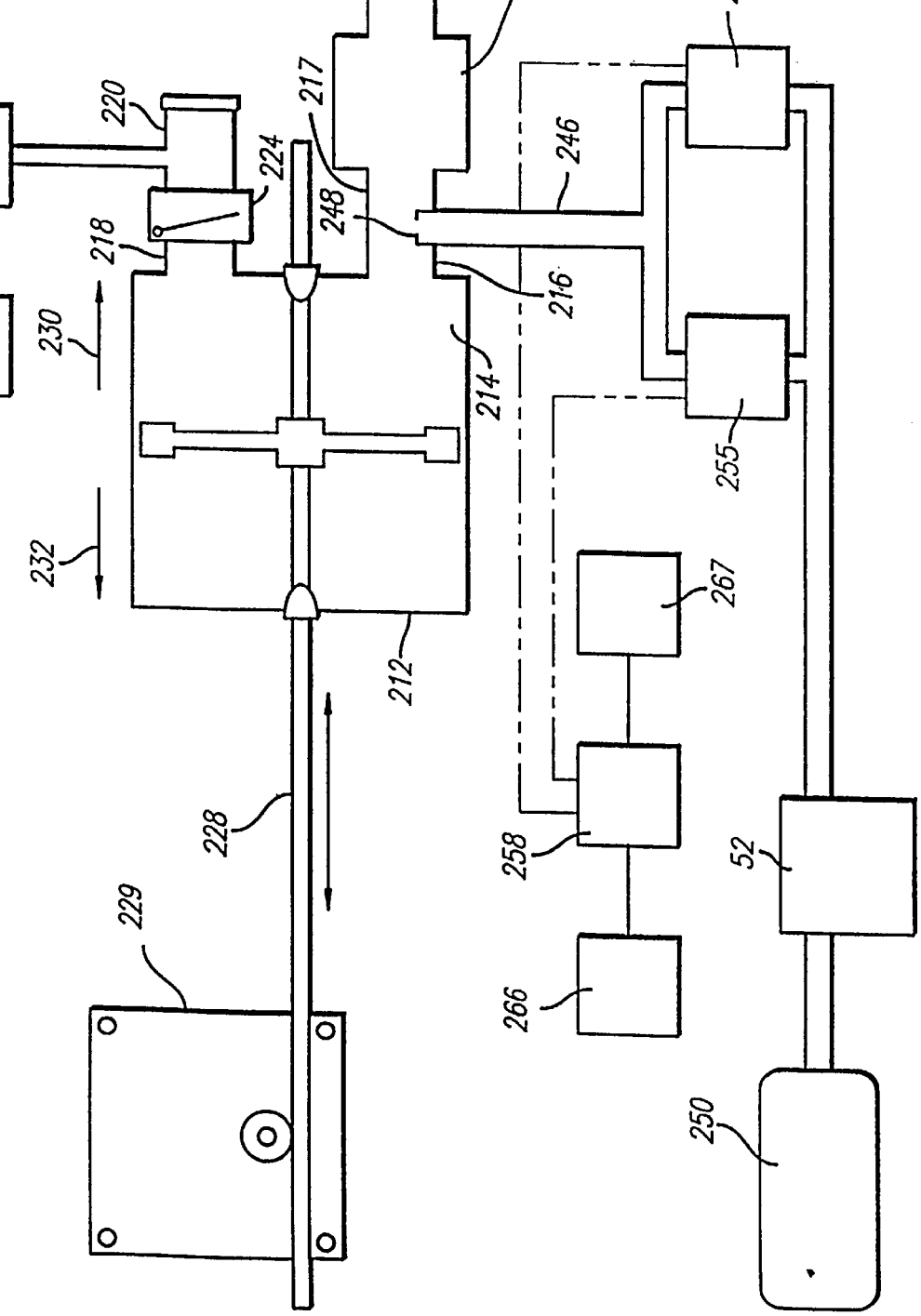
FIG. 5 shows another preferred embodiment of the gas mixing apparatus of the invention in which the selected gas and air are introduced into the manifold to the gas mixing chamber.

With reference to FIG. 5, in a third preferred embodiment, the gas mixing apparatus 210 includes a fixed volume piston chamber 212 with a gas delivery portion 214, an inlet 216 for receiving mixed gas, and an outlet 218 for delivering mixed gas to the patient airway 220. The outlet preferably includes a check valve 224 allowing mixed gas to flow only to the patient airway. A reciprocating piston 226 is mounted within the piston cylinder to piston rod 228 that can in turn be driven, for example, by a rack and pinion motor 229. The piston is movable between an extended position 230 in the gas delivery portion 214 of the piston chamber and a retracted position 232. An air inlet 236 open to the atmosphere can also advantageously be connected to the piston chamber inlet 216 through one or more enlarged air capacitor chambers 237. The piston chamber inlet 216 also preferably includes a flow limiting inlet 246 having a sonic flow limiting orifice 248 for admitting the selected gas to the gas mixing chamber. Alternatively, the inlet 246 can admit the selected gas directly to the piston chamber as the piston retracts. Gas mixing occurs in the manifold 217 of the piston chamber inlet 216 and in the piston chamber itself as the selected gas and air are admitted to the piston chamber, eliminating the requirement for a separate reservoir, and thereby making the gas mixing apparatus considerably more compact.

A source 250 of the selected gas is also provided, such as a tank of pressurized oxygen, for example, connected in fluid communication to the gas pressure regulating means 52 for regulating the pressure of the gas supplied from the selected gas source. The pressure regulating means 52 shown in FIG. 5 is substantially identical to the pressure regulating means 52 of FIG. 1 and can equally comprise the demand valve arrangement 52 and blender 80 as described above with reference to FIG. 3. Valve means 254, such as a solenoid valve or plurality of solenoid valves, is also provided between the pressure regulating means 52 and the flow limiting inlet 246 for regulating the flow of the selected gas to the piston chamber. The valve means is switchable between an open position in which the selected gas flows to the gas mixing chamber, and a closed position in which the selected gas is prevented from flowing to the gas mixing chamber. A control unit 258, typically connected to sensors (not shown) for monitoring the patient breathing cycle, is also preferably provided for controlling the valve means 254 to admit the selected gas to the gas mixing chamber during at least one interval of time during at least a portion of the breath cycle for a total period of time to obtain a selected proportion of the selected gas in the mixed gas, typically preset or selected through the control unit. Introduction of the selected gas and air into a gas delivery chamber can thus be sequenced in the mixing cycle, during retraction of the piston to draw breathing gas into the piston chamber, with a pulse of the selected gas followed by a pulse of air, to insure that the selected gas will enter the piston chamber first, to facilitate adequate mixing of the selected gas and air in the manifold and in the piston chamber for delivery to a patient.

The solenoid valve is typically opened for a sufficient time to supply the desired proportion of oxygen in the mixed gas supplied to the piston chamber. The flow limiting inlet to the gas mixing chamber preferably permits the supply of a mass flow rate equal to the mass flow rate produced by the retracting piston. The movement of the reciprocating piston in the piston chamber is controlled by the control unit 258 to deliver a quantity of mixed gas in the desired volume at the desired pressure to a patient. The concentration of the selected gas can be corrected for atmospheric changes by sensing atmospheric pressure changes with a pressure sensor 266, and for temperature changes measured by a temperature sensor 267, and a microprocessor, for example, that is responsive to signals from the pressure sensor and temperature sensor to adjust the time that the solenoid valve is switched open. If the oxygen supply runs out, or the valve means is stuck in a closed position, air can still be provided to the piston from the air capacitor chambers. However, a sensor 262 of the concentration of the selected gas can also be connected with the outlet 218 or the patient airway 220, for example, to operate an alarm 264 to alert an operator so that such a problem can be detected and corrected.

In the method of the invention for mixing gas for a ventilator system for supplying mixed gas to a patient airway during an inspiratory portion of a breath cycle, a supply flow of the selected gas, such as oxygen, is provided to the gas mixing chamber means, either a reservoir in the first embodiment of the apparatus, or the gas mixing chamber in piston chamber, in the second preferred embodiment of the apparatus. The piston is extended in the piston chamber to deliver a flow of mixed gas from the gas delivery portion of the piston chamber to the patient airway, and is then retracted in a continuing cycle to draw gas into the gas delivery portion of the piston chamber. The method of the invention provides for providing the supply flow of the selected gas to the reservoir means to admit the selected gas to the reservoir means during at least one interval of time period during the breath cycle to minimize peak flow rate of the supply flow, and for a total period of time to obtain a selected proportion of the selected gas in the mixed gas. The selected gas can, for example, be admitted intermittently or continuously during one, or multiple opening periods during the period of retraction of the piston. Some of the selected gas can also be admitted to the gas mixing chamber means before the piston starts retraction as well, to reduce peak flow rate of the selected gas supply, since this will allow the total amount of time during a breath cycle that the selected gas is admitted to the gas mixing chamber to be longer. Thus, while the selected gas is typically admitted to the gas mixing chamber means during retraction of the piston, when the mixed gas is drawn into the delivery side of the piston chamber, the selected gas can also be admitted to the gas mixing chamber means during extension of the piston to deliver mixed gas to the patient airway, to allow a reduction of the minimum peak flow of the supply flow of the selected gas. The mixed gas is then conducted to a displacement side of the piston chamber, and delivered to a patient airway by extension of the piston in the piston chamber.

The selected gas and air can be mixed sequentially in alternating pulses, and can thus be sequenced in the mixing cycle, during retraction of the piston to draw breathing gas into the chamber in which the gases are to be mixed. It is particularly advantageous to provide a pulse of the selected gas followed by a pulse of air, to insure that the selected gas will not escape from the chamber in which the gases are to be mixed, and to facilitate adequate mixing of the selected gas and air. Thus, for example, the selected gas and air can be introduced into the chamber in which they are to be mixed in a plurality of pairs of pulses comprising a pulse of the selected gas followed by a pulse of air. Alternatively, a plurality of pulses of the selected gas can be interspersed during drawing of air and selected gas into the chamber in which they are to be mixed.

It should be recognized that the demand valve and mechanically variable resistance blender configuration can be connected to deliver gas directly to the piston cylinder, to one or more reservoirs for the piston cylinder, or to a manifold leading to the piston cylinder, in place of the sonic flow limiting orifices described above.

It has thus been demonstrated that the present invention provides for a gas mixing apparatus that regulates the pressure of a selected gas to approximately ambient atmospheric pressure, for mixing with air at ambient atmospheric pressure for use as a breathing gas in a ventilator. The pressure of the selected gas is limited to a maximum pressure, so that even if a valve for admitting the selected gas for mixing at ambient pressure fails, breathing gas delivered to the patient will not reach an excessive pressure. The invention further allows a desired sequencing of introduction of the gases to be mixed into a chamber of the ventilator in which the gases are to be mixed, to facilitate adequate mixing.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for mixing gas for a ventilator system for supplying mixed gas to a patient airway during an inspiratory portion of a breath cycle, said ventilator system including a pump chamber, a gas displacement member disposed within said pump chamber, the gas displacement member being moveable between first and second positions, the method comprising the steps of:

mixing a first selected gas with a second selected gas to provide mixed gas for the pump chamber;

moving the gas displacement member between said first position and said second position to deliver a flow of mixed gas from the pump chamber to the patient airway, and to draw mixed gas into the pump chamber.

2. The method of claim 1, further comprising the step of minimizing peak flow rate of the first selected gas.

3. The method of claim 1, wherein said step of mixing comprises sequentially supplying said first selected gas in at least one pulse of predetermined amplitude and duration, followed by supplying air for mixing said air with said first selected gas.

4. The method of claim 1, wherein said step of mixing comprises sequentially supplying said first selected gas in a plurality of pulses, with each said pulse followed by supply of air for mixing said air with said first selected gas.

* * * * *